United States Patent
Sun et al.

(10) Patent No.: US 8,105,844 B2
(45) Date of Patent: Jan. 31, 2012

(54) APPARATUS AND METHOD OF USING POROUS MATERIAL FOR ANTIGEN SEPARATION, IDENTIFICATION, AND QUANTIFICATION WITH ELECTROPHORESIS TECHNIQUES

(75) Inventors: Zhen Hong Sun, Shanghai (CN); Tao Pan, Shanghai (CN); Wendy Wang, Shanghai (CN); Xuanbin Liu, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 587 days.

(21) Appl. No.: 12/123,714

(22) Filed: May 20, 2008

(65) Prior Publication Data

US 2009/0288953 A1    Nov. 26, 2009

(51) Int. Cl.
    *G01N 33/563* (2006.01)
(52) U.S. Cl. ...................................................... 436/516
(58) Field of Classification Search .................. None
    See application file for complete search history.

(56) References Cited

U.S. PATENT DOCUMENTS

| | | | | | |
|---|---|---|---|---|---|
| 4,526,690 | A | * | 7/1985 | Kiovsky et al. | 210/335 |
| 4,628,035 | A | * | 12/1986 | Tokinaga et al. | 435/7.94 |
| 4,824,778 | A | * | 4/1989 | Nagai et al. | 435/7.92 |
| 5,212,988 | A | * | 5/1993 | White et al. | 73/599 |
| 6,475,805 | B1 | * | 11/2002 | Charm et al. | 436/514 |
| 6,902,889 | B1 | * | 6/2005 | Carlsson et al. | 435/6 |
| 7,326,326 | B2 | * | 2/2008 | Chang et al. | 204/546 |
| 2002/0198567 | A1 | * | 12/2002 | Keisari et al. | 607/3 |
| 2003/0129597 | A1 | * | 7/2003 | Nguyen | 435/6 |
| 2004/0115707 | A1 | * | 6/2004 | Amano | 435/6 |
| 2008/0156648 | A1 | * | 7/2008 | Dudziak et al. | 204/543 |

OTHER PUBLICATIONS

Charles H. Zierdt, "Adherence of Bacteria, Yeast, Blood Cells, and Latex Spheres to Large-Porosity Membrane Filters", Applied and Environmental Microbiology, Dec. 1979, vol. 38, No. 6, pp. 1166-1172.

Meera J. Desai et al., "Separation, Identification, and Characterization of Microorganisms by Capillary Electrophoresis", Microbiology and Molecular Biology Reviews, Mar. 2003, vol. 67, No. 1, pp. 38-51.

J. R. Glynn, Jr. et al., "Capillary Electrophoresis Measurements of Electrophoretic Mobility for Colloidal Particles of Biological Interest", Applied and Environmental Microbiology, Jul. 1998, vol. 64, No. 7, pp. 2572-2577.

Pierre N. Floriano et al., "Membrane-based on-line optical analysis system for rapid detection of bacteria and spores", Biosensors and Bioelectronics 20 (2005), pp. 2079-2088.

* cited by examiner

*Primary Examiner* — Ann Lam
(74) *Attorney, Agent, or Firm* — Munck Carter, LLP

(57) ABSTRACT

An apparatus includes a porous membrane for retaining antigens from a sample as the sample passes through the membrane. The apparatus also includes a first binding region within the membrane. The first binding region includes antibodies associated with a first antigen of interest. At least some of the antigens retained in the membrane are brought into contact with the first binding region by applying an electrophoresis field across the membrane. The porous membrane could also include an electrophoresis buffer. A presence of the first antigen of interest could be detected by exposing the first binding region to a chemiluminescent reagent, and a quantity of the first antigen of interest could be determined by performing a chemiluminescent assay on the binding region.

20 Claims, 8 Drawing Sheets

APPARATUS AND METHOD OF USING POROUS MATERIAL FOR ANTIGEN SEPARATION, IDENTIFICATION, AND QUANTIFICATION WITH ELECTROPHORESIS TECHNIQUES

TECHNICAL FIELD

This disclosure relates generally to antigen separation, identification, and quantification and more specifically to an apparatus and method of using porous material for antigen separation, identification, and quantification with electrophoresis techniques.

BACKGROUND

Antigens typically include bacteria, viruses, and other organisms or materials that can invoke an immune response. Antigens often pose a potential risk to human health, such as when the antigens are present in food, water, and air supplies. Therefore, the detection and quantification of such antigens is often an important or necessary function in various situations.

Current methods of detecting antigens are often time-consuming or costly. For example, for microorganism contaminations, cell culture and biochemical methodologies may take days to weeks before results are obtained. Methods such as solid phase cytometry (SPC), polymerase chain reaction (PCR), surface plasmon resonance (SPR), and similar techniques detect antigens based on surface proteins or nucleotide detection. While such methods may detect antigens in minutes to hours, these methods are costly, require manual work, or have limited detection capabilities.

Another significant drawback to all of the above methods is that they are typically difficult to implement in an on-line manner. These methods usually require that an antigen of interest first be concentrated using membrane filtration or other devices. A condensate then often needs to be collected from the filter, or the antigen of interest needs to be labeled on the membrane prior to the measurement.

SUMMARY

This disclosure provides an apparatus and method of using porous material for antigen separation, identification, and quantification with electrophoresis techniques.

In a first embodiment, an apparatus includes a porous membrane for retaining antigens from a sample as the sample passes through the membrane. The apparatus also includes a first binding region within the membrane, where the first binding region includes antibodies associated with a first antigen of interest. At least some of the antigens retained in the membrane are brought into contact with the first binding region by applying an electrophoresis field across the membrane.

In particular embodiments, the porous membrane retains the antigens from the sample in a vertical direction.

In other particular embodiments, the apparatus includes a second binding region within the porous membrane. The second binding region includes antibodies associated with a second antigen of interest.

In yet other particular embodiments, the porous membrane comprises a material selected from the group consisting of polyvinylidene fluoride (PVDF), cellulose acetate (CA), polyether sulfone (PES), polysulfone (PS), and polyamide (PA).

In still other particular embodiments, the porous membrane is hydrophilic and low protein binding, has a protein binding upper limit of 40-1000 ng/cm$^2$ and a pore size from 0.2 µm to 10 µm.

In a second embodiment, a system includes a porous membrane and a binding region within the porous membrane. The binding region includes antibodies associated with an antigen of interest. The system also includes a voltage source for creating an electrophoresis field to move a plurality of antigens from a first area of the porous membrane to a second area of the porous membrane such that the antigens come into contact with the binding region. The system further includes a detector for detecting if the antigen of interest is present in the binding region.

In a third embodiment, a method includes adding a sample to a chamber at one area of a porous membrane. The porous membrane includes a first binding region having antibodies associated with a first antigen of interest. The method also includes applying an electrophoresis field across the porous membrane. The antigens contained in the sample move across the porous membrane and come into contact with the first binding region. The method further includes detecting if the first antigen of interest is present in the first binding region.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 8, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
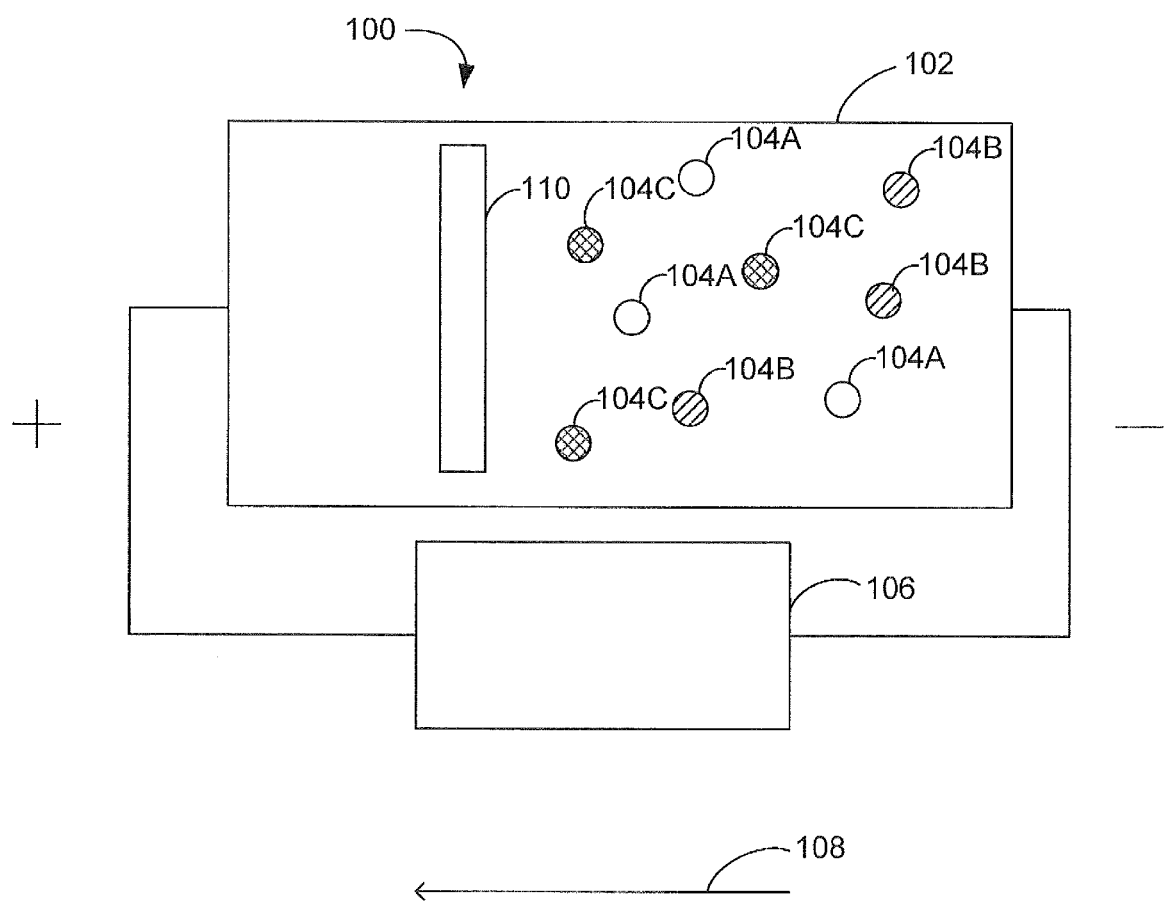
FIG. 1 illustrates an example separation system before separation of antigens has occurred according to this disclosure.

FIG. 1 illustrates an example separation system 100 according to this disclosure. The embodiment of the separation system 100 shown in FIG. 1 is for illustration only. Other embodiments of the separation system 100 could be used without departing from the scope of this disclosure.

As shown in FIG. 1, the separation system 100 includes a porous membrane 102. In this example, a plurality of antigens 104A, 104B, and 104C are shown within the porous membrane 102. Antigens 104A represent a first antigen, antigens 104B represent a second antigen, and antigens 104C represent a third antigen (collectively referred to as "antigens 104"). A high-voltage power supply 106 creates a high-voltage external electrophoresis field across the porous membrane 102.

Figure 2:
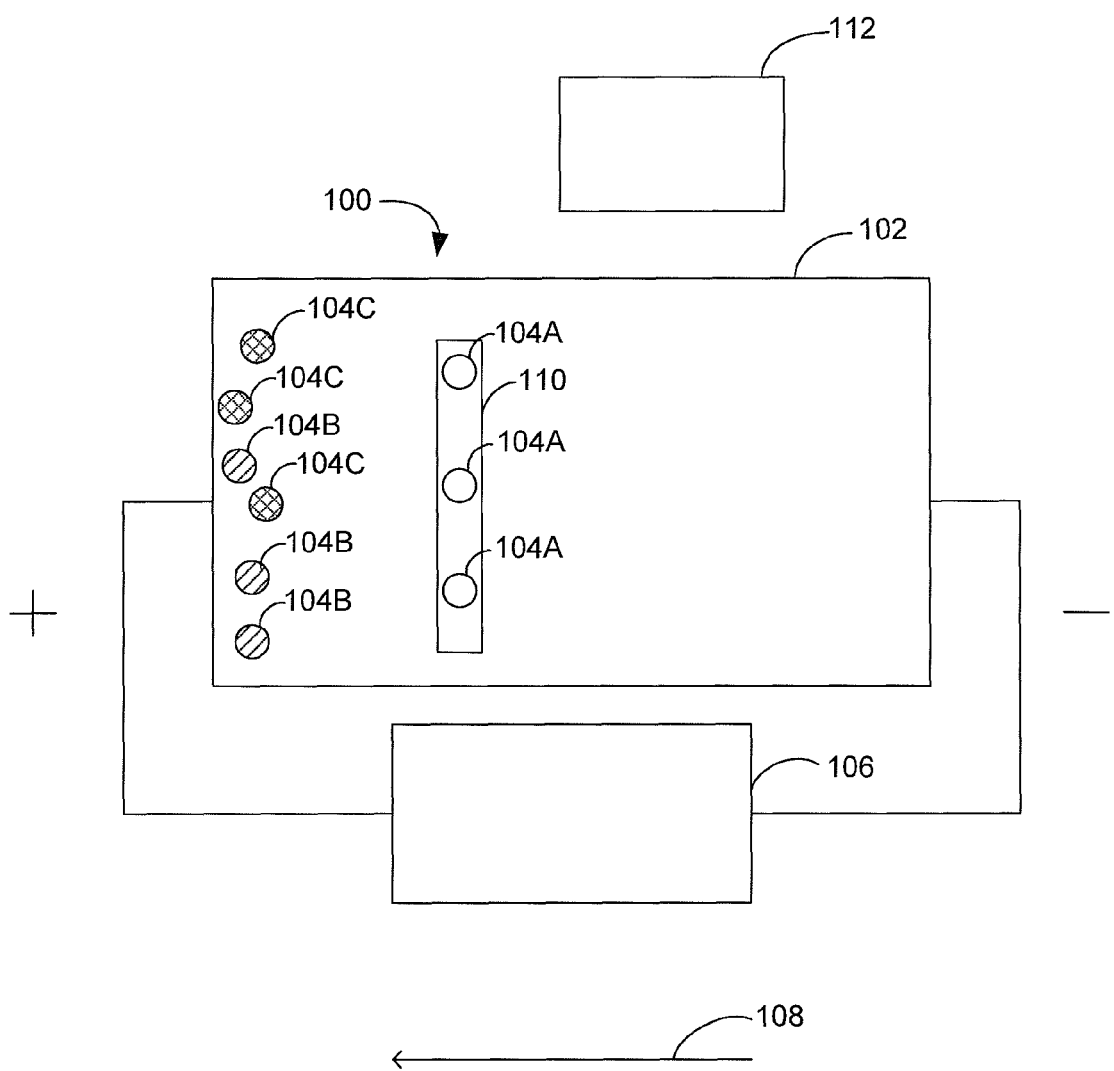
FIG. 2 illustrates an example separation system after separation of antigens has occurred according to this disclosure.

The antigens 104 may be mixed with an electrophoresis buffer prior to being placed in the separation system 100, or the antigens 104 could be mixed with an electrophoresis buffer that is already present in the porous membrane 102. Because the antigens 104 carry a negative charge after they are mixed with an electrophoresis buffer, the antigens 104 move to the positively charged end of the porous membrane 102. The porous membrane 102 allows the antigens 104 to pass through conjoined pores without allowing the antigens 104 to pass along the surface. As the antigens 104 move to the positively charged end of the membrane 102 as indicated by an arrow 108, the antigens 104 come into contact with a binding region 110, which contains a plurality of immobilized antibodies specific for an antigen of interest. In this example, the antigen of interest is the antigens 104A. As shown in FIG. 2, as the antigens 104 come into contact with the binding region 110, the antibodies specific for the antigens 104A bind the antigens 104A while allowing the antigens 104B and 104C to pass. Accordingly, the separation system 100 can use antigen-specific antibodies to identify the antigens 104A, as well as to separate the antigens 104A from the antigens 104B and 104C.

The electrophoresis buffer could be existing or modified basic buffer, like Tris-boric acid-EDTA buffer or MOPS buffer. In some embodiments, to facilitate the antigen's migration across the membrane, proper additives like poly (ethylene oxide) could be added in the buffer to reduce adsorption or other reactions between the antigen and the porous membrane 102.

In an embodiment, the porous membrane 102 could be selected from existing membrane products used in industrial, laboratory or medical areas with hydrophilic and low protein binding properties. For example, the porous membrane 102 may comprise materials such as polyvinylidene fluoride (PVDF), cellulose acetate (CA), polyether sulfone (PES), polysulfone (PS), polyamide (PA) etc. Also, the porous membrane may have a protein binding upper limit of 40-1000 ng/cm$^2$. In some embodiments, the porous membrane 102 could be treated partially or completely with proper chemicals to facilitate its use for antibody immobilization in certain areas and reduce antigen adherence during electrophoresis. In other embodiments, the pore size of the porous membrane could be in the scale from 0.2 to 10 μm, fit for antigen retainment and migration when the electric field is applied. In further embodiments, the porous membrane is kept stable in the electrophoresis buffer when the electric field is applied, and adsorption or other reactions between the antigen and the porous membrane is kept low.

Moreover, in some embodiments, the high voltage and the electrophoresis buffer will not affect the antigen's activity compared with other methodologies such as separation by capillary electrophoresis.

The antigens 104 can be any type of organism that is capable of being bound by an antibody. For example, the antigens 104 may be microbes such as bacteria, archaebacteria, fungi, protista, or viruses.

As shown in FIG. 2, once the antigen of interest (antigens 104A) is bound by binding region 110, a detection system 112 is used to detect the presence of the antigens 104A on-site. The presence of the antigens 104A may be detected by any method known to one of ordinary skill in the art. For example, the presence of the antigens 104A may be detected by a chemiluminescence assay, such as a luciferin-luciferase assay. In this example, an ATP-releasing buffer is sprayed in the binding region 110.

Because all living organisms produce ATP, the ATP-releasing buffer will cause any antigen of interest bound in the binding region 110 to release ATP. Luciferin-luciferase reagent then is sprayed in the binding region 110. If the antigen of interest is bound in the binding region 110, chemiluminescence will be produced once the luciferin-luciferase complex meets and consumes the released ATPs.

If chemiluminescence is detected by the detection system 112, an amount or quantity of the antigens 104A in the binding region 110 can be determined by recording and analyzing the chemiluminescence data collected from the luciferin-luciferase assay. The use of antibodies to bind the antigens 104A has the added benefit of ensuring the activity of the antigens 104A. Special antibodies, which only bind biologically active antigens, may be chosen. This eliminates the concern of detecting and quantifying biologically-inactive antigens.

Figure 3:
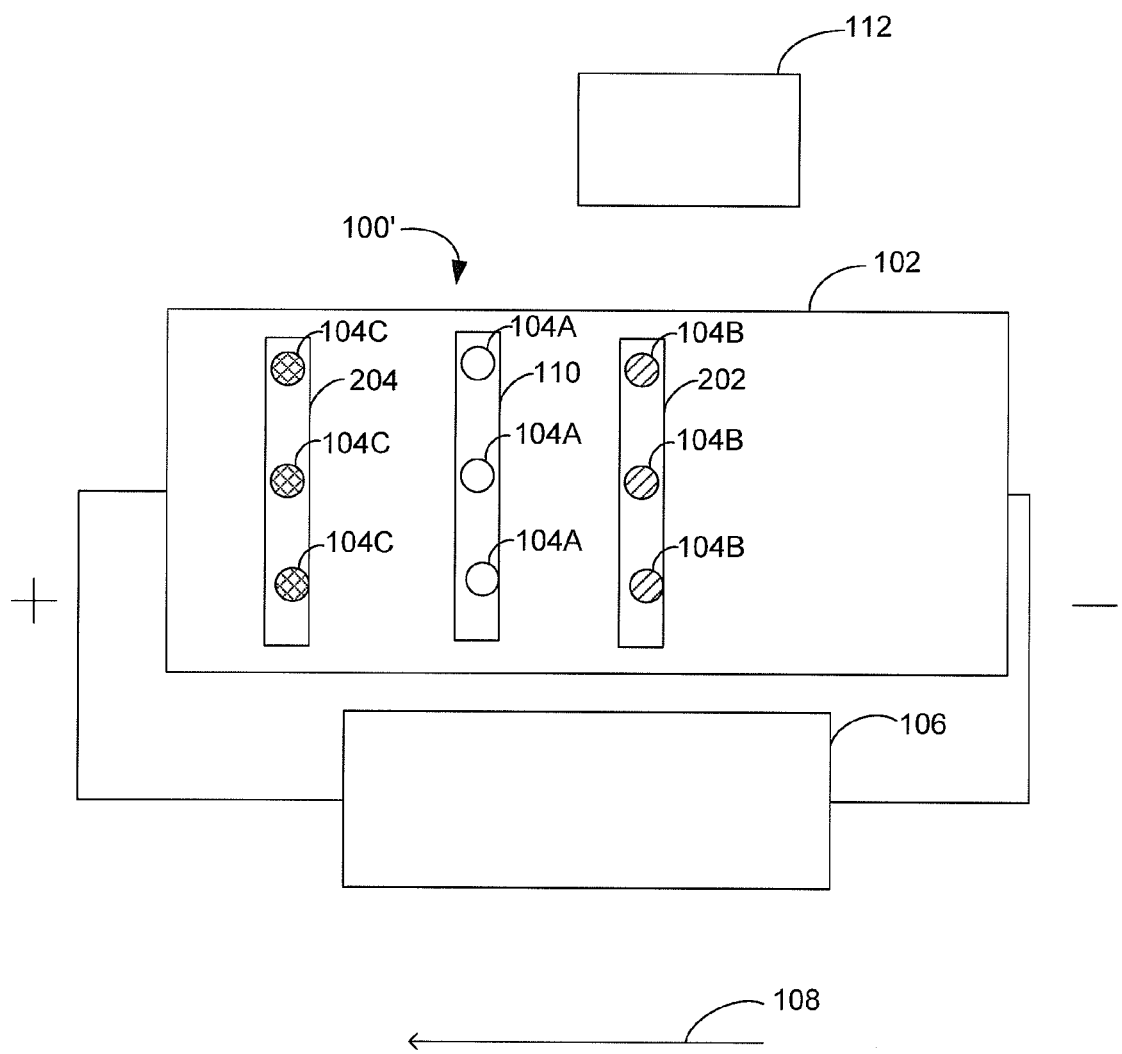
FIG. 3 illustrates an example separation system with multiple binding regions according to this disclosure.

Although the above examples describe the separation system 100 as having a single binding region, one of ordinary skill in the art would recognize that the separation system 100 could have any number of binding regions. FIG. 3 illustrates an example separation system 100' having multiple binding regions. In this example, the separation system 100' has a binding region 202 that is specific for the antigens 104B. The separation system 100' also has a binding region 204 that is specific for the antigens 104C. This particular embodiment of the separation system 100' allows for multiple antigens of interest to be separated and detected at the same time, saving time and cost. Once the antigens 104 have been bound by their respective binding regions, the presence and amount or quantity of the antigens 104 in each binding region could then be determined by the detection system 112 as described earlier.

Although the binding regions are shown as being specific for different antigens, one of ordinary skill in the art would recognize that multiple binding regions may be specific for the same antigen of interest. Having more than one binding region for the same antigen of interest may be advantageous, for example, when the antigen of interest is present in large amounts such that there is not enough antibodies in a single binding region to bind a significant number of the antigen of interest (the binding region becomes saturated). In this case, having more than one binding region could provide a more accurate measurement of the quantity of antigens present in a sample. Having more than one binding region for the same antigen of interest may also be advantageous when the antigen of interest is present in a small amount. In this case, having more than one binding site increases the ability of detecting the antigen of interest.

Furthermore, although the binding regions are illustrated as being rectangular in shape, one of ordinary skill in the art would recognize that the binding regions can take on any number of shapes and can be located at any number of places within the porous membrane. For example, the binding region may take the shape of a ring in the center of the porous membrane.

Figure 4:
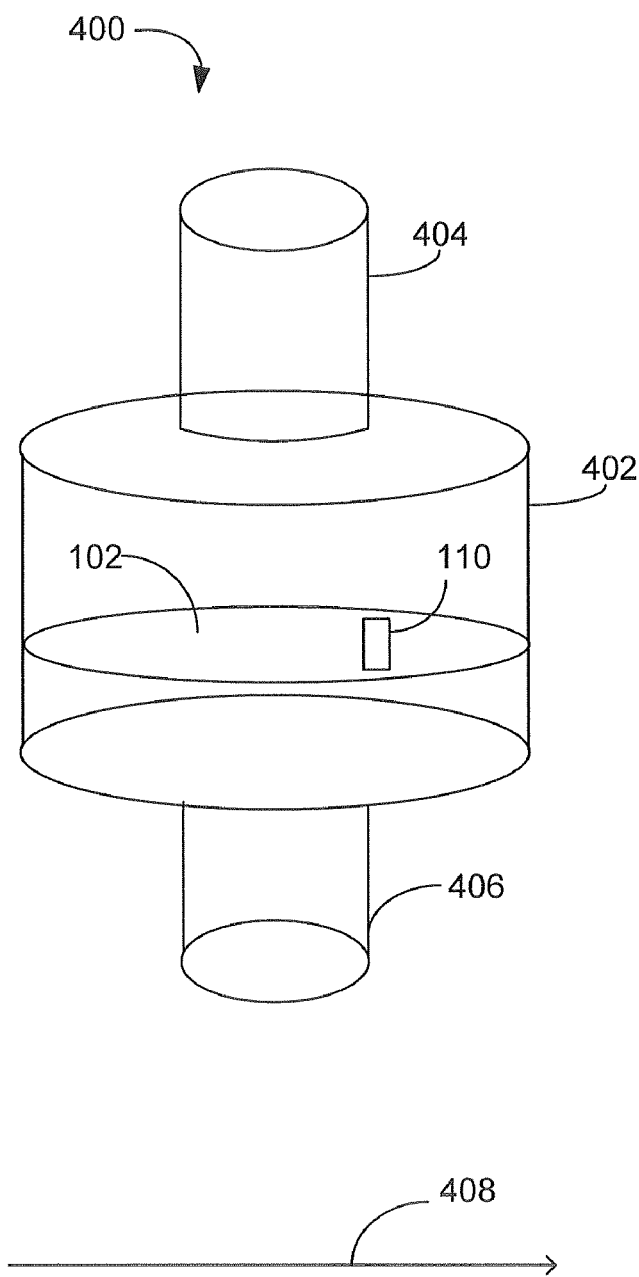
FIG. 4 illustrates an example on-line separation system according to this disclosure.

FIG. 4 illustrates an example on-line separation system 400. In this example, a sample is introduced into a chamber 402 by way of an inlet 404. The sample then comes into contact with the membrane 102. The membrane 102 serves to hold back antigens in the sample. The rest of the sample may then exit the chamber 104 by way of an outlet 406. An electrophoresis buffer is added to the membrane 102 before, after, or currently with the sample. As described earlier, antigens held by the membrane 102 may carry a negative charge due to the electrophoresis buffer. A high-voltage external electrophoresis field is created across the membrane 102. The high-voltage external electrophoresis field causes the antigens held by the membrane 102 to move towards the area of the membrane 102 that carries a positive charge. The direction of the movement is indicated by an arrow 408. As the antigens move towards the area of the membrane 102 that carries a positive charge, the antigens come into contact with the binding region 110.

As described earlier, the antibodies in the binding region 110 bind the antigen that they are specific for (the antigen of interest), while allowing other antigens to pass. Once the antigen of interest has been bound by the binding region 110, the presence and the quantity of the antigens in the binding region 110 can be determined by a detection system 112 as described earlier. In some embodiments, the detection system 112 could include a reagent spraying unit and an optical detection unit integrated with the chamber 402.

As discussed earlier with respect to FIG. 3, the membrane 102 shown in FIG. 4 could have any number of binding regions 110 that are specific for the same or different antigens. Also, the binding regions can take on any number of shapes and can be located at any number of places within the porous membrane.

In this example, the membrane 102 serves as a medium for electrophoresis. Also, the membrane 102 serves to concentrate the antigens in a vertical direction so that the antigens are perpendicular to the direction of the electrophoresis. Using the membrane 102 to concentrate the antigens can help to reduce or eliminate the need to concentrate the antigens through a filter or matrix and the need to extract or elude the antigens from the filter or matrix. However, in most case, prefiltration is still needed to remove large particles in the liquid or air samples before the concentration steps. By this means, potential clogs in the concentration steps can be avoided.

Figure 5:
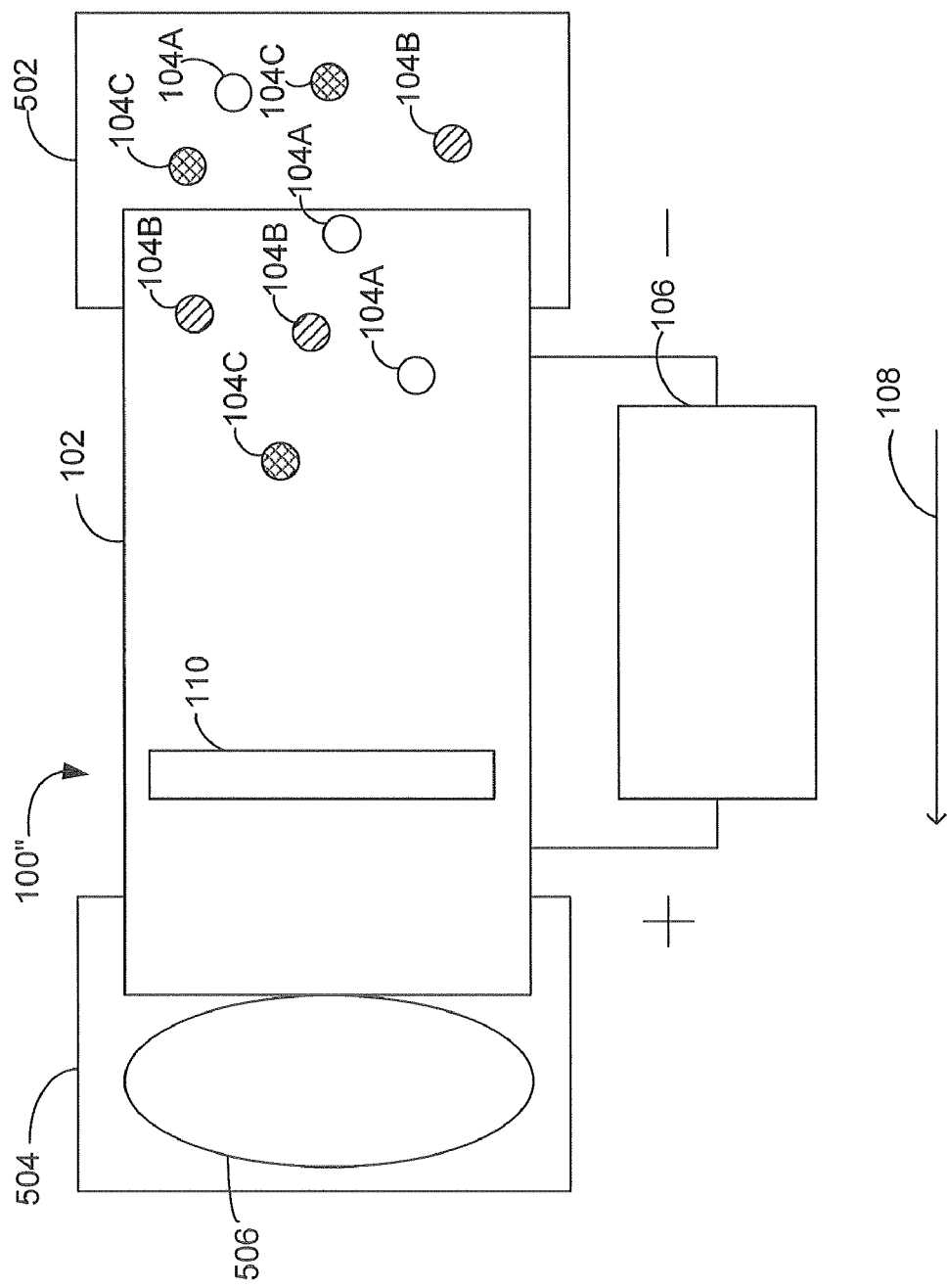
FIG. 5 illustrates an example off-line separation system before separation of antigens has occurred according to this disclosure.

Although FIG. 4 illustrates an example implementing the separation system 400 in an on-line manner, the separation system 400 also could be used in an off-line manner with samples that have already gone through the process of concentration and elution. An example of a system 100" operating in an off-line manner is shown in FIG. 5. In this example, a sample that has been concentrated and eluded is mixed with an electrophoresis buffer using a proper ratio, which causes antigens in the sample to carry a negative charge. The sample then is placed into a sample chamber 502, which is located at one end of the porous membrane 102. At the other end of the porous membrane 102 is a receiving chamber 504. Once the sample has been placed into the sample chamber 502, the high-voltage power supply 106 applies a high-voltage external electrophoresis field across the porous membrane 102.

Figure 6:
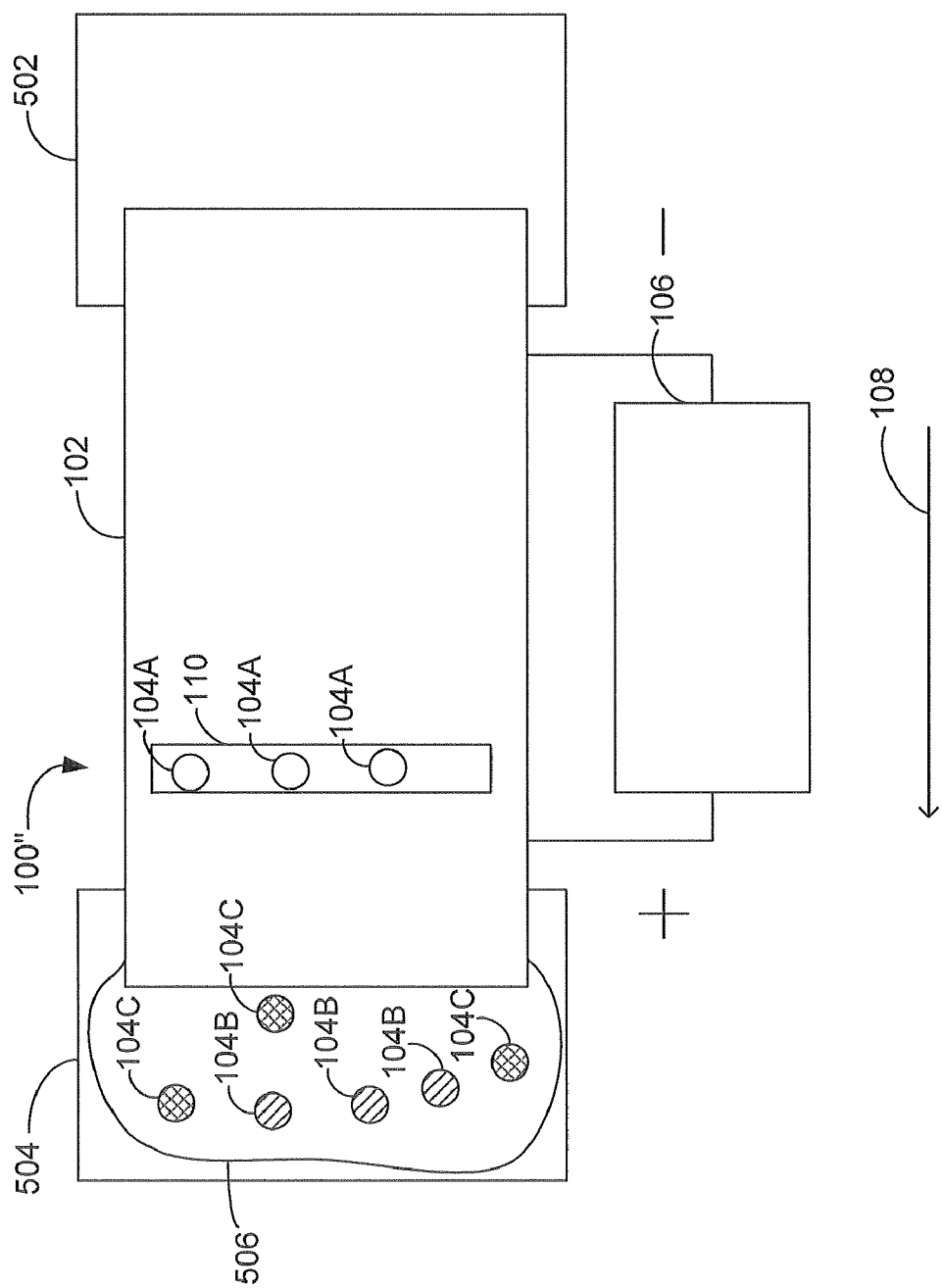
FIG. 6 illustrates an example off-line separation system after separation of antigens has occurred according to this disclosure.

Because the antigens 104 carry a negative charge after they are mixed with the electrophoresis buffer, the antigens 104 move to the positively charged end of the porous membrane 102, coming into contact with the binding region 110. In this example, the antigen of interest is the antigens 104A. As shown in FIG. 6, as the antigens 104 come into contact with the binding region 110, the antibodies specific for antigens 104A bind the antigens 104A while allowing the antigens 104B and 104C to pass.

As shown in FIG. 6, once the antigen of interest is bound by binding region 110, the detection system 112 is used to detect the presence of the antigens 104A on-site. As established earlier, the presence of the antigens 104A may be detected by any method known to one of ordinary skill in the art. For example, the presence of the antigens 104A may be detected by a chemiluminescence assay, such as luciferin-luciferase assay.

In some embodiments, the receiving chamber 504 includes a water absorbent material 506 to keep the membrane 102 filled with enough electrophoresis buffer and facilitate the directional flow of the electrophoresis buffer inside the membrane 102. As discussed earlier with respect to FIGS. 3 and 4, the membrane 102 shown in FIGS. 5 and 6 could have any number of binding regions that are specific for the same or different antigens. Also, the binding regions can take on any number of shapes and can be located at any number of places within the porous membrane.

Figure 7:
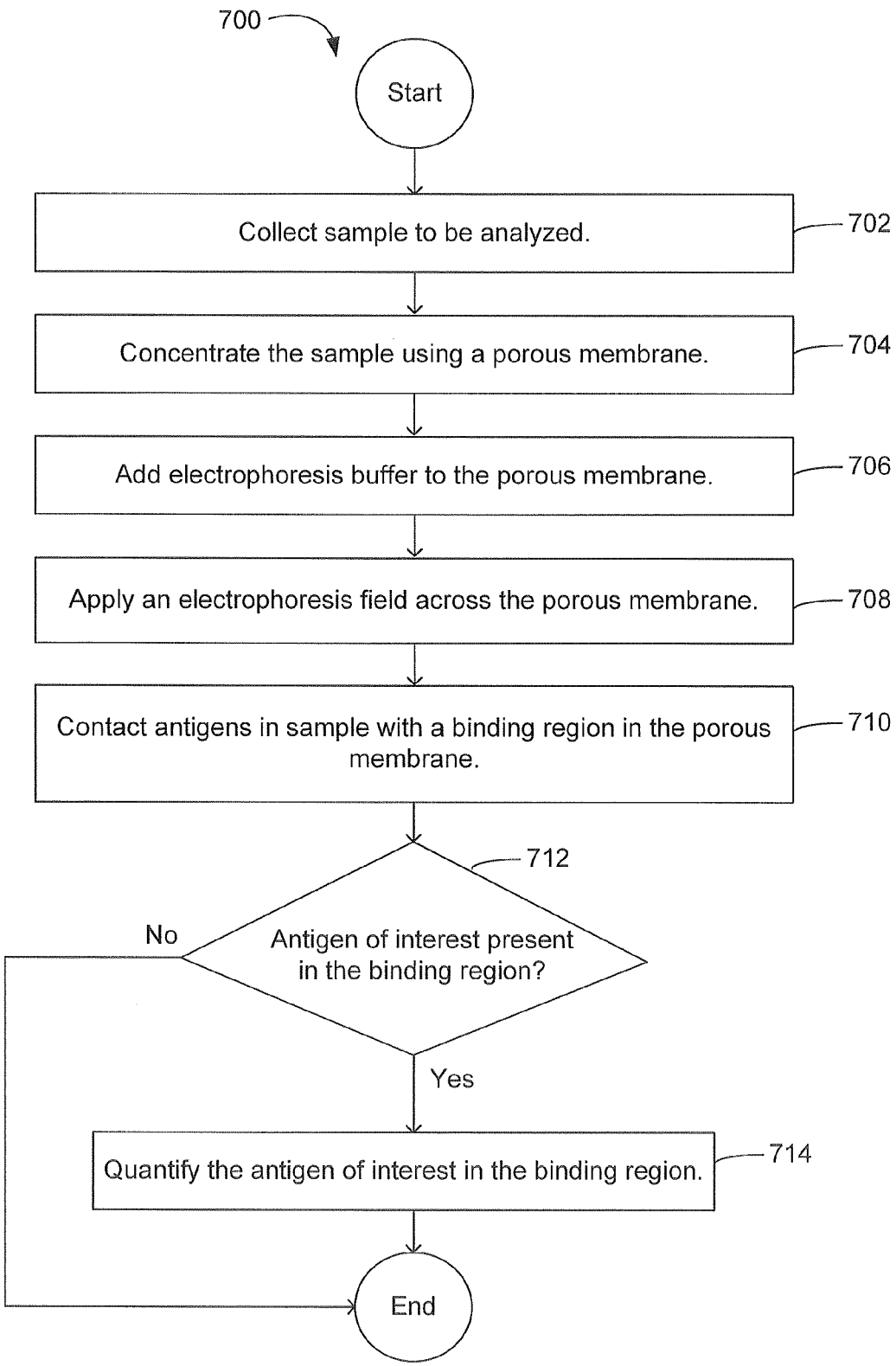
FIGS. 7 and 8 illustrate example methods for separating, detecting, and quantifying antigens according to this disclosure.
Figure 8:
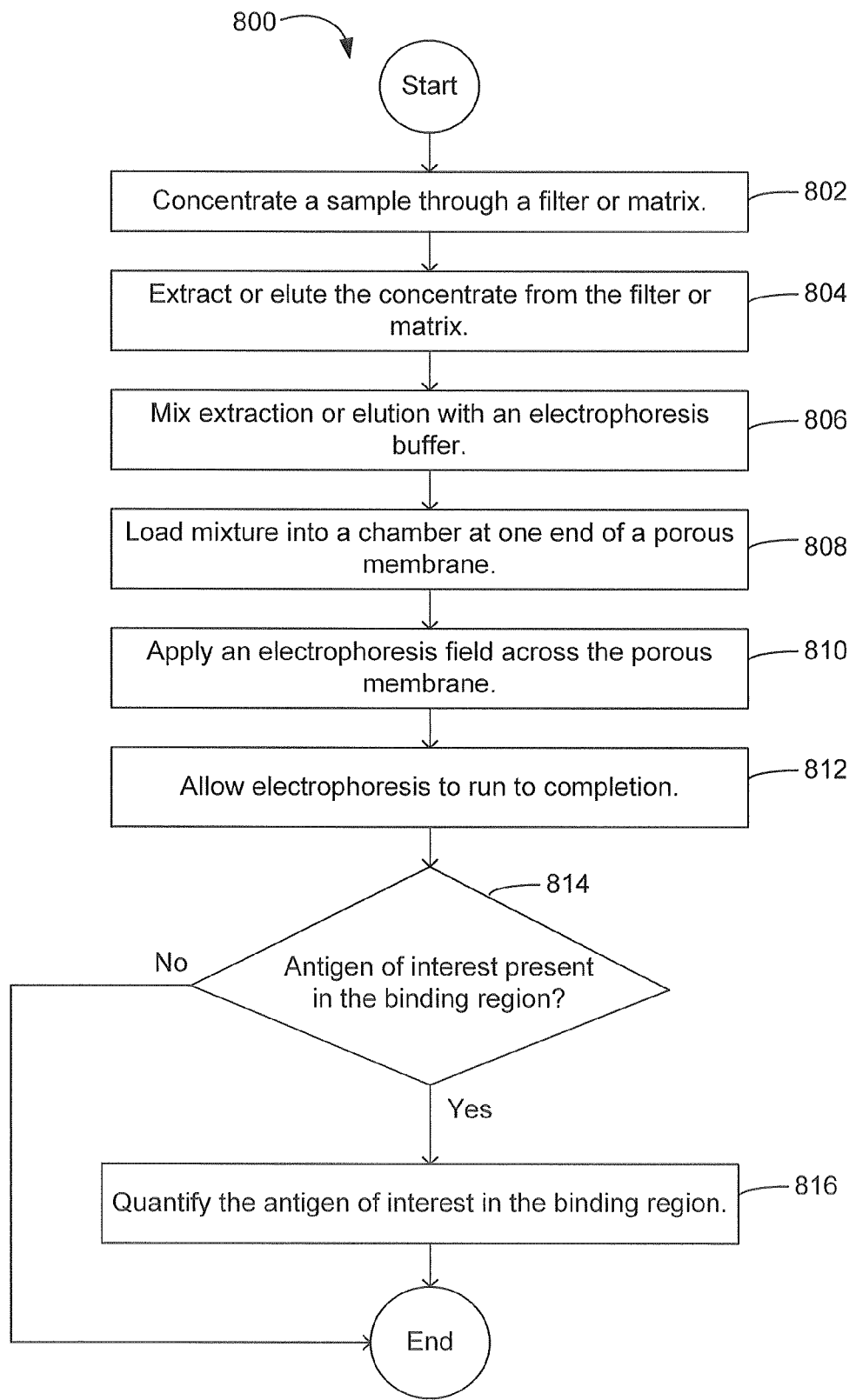

FIGS. 7 and 8 illustrate example methods for identifying, detecting, and quantifying antigens in a sample according to this disclosure. The embodiments of the methods shown in FIGS. 7 and 8 are for illustration only. Other embodiments of the methods could be used without departing from the scope of this disclosure.

As shown in FIG. 7, an on-line method 700 includes collecting a sample to be analyzed at step 702. The sample may be, for example, in the form of an air sample or a liquid sample. The sample is concentrated using a porous membrane at step 704. This could include, for example, introducing the sample into the chamber 402 by way of the inlet 404 and concentrating the sample in the vertical direction using the porous membrane 102. An electrophoresis buffer is added to the porous membrane at step 706. A high-voltage external electrophoresis field is applied across the porous membrane at step 708. The electrophoresis field could be created, for example, by the high-voltage power supply 106.

Because the antigens in the sample carry a negative charge upon mixing with the electrophoresis buffer, the antigens in the sample move towards the positive end of the porous membrane created by the high-voltage external electrophoresis field. As the antigens move towards the positive end of the porous membrane, the antigens in the sample come into contact with a binding region that contains antibodies specific for an antigen of interest at step 710. The binding region could be, for example, the binding region 110. The binding region is analyzed for the presence of the antigen of interest at step 712. The presence of the antigen of interest could be detected, for example, by spraying an ATP-releasing buffer and luciferin-luciferase reagent on the binding region. If the presence of the antigen of interest is detected, the quantity of the antigen of interest in the binding region is quantified at step 714. The quantity of the antigens in the binding region can be determined, for example, by recording and analyzing chemiluminescence data collected from luciferin-luciferase assay.

As shown in FIG. 8, an off-line method 800 includes concentrating a sample through a filter or matrix that holds back or absorbs antigens in the sample at step 802. The concentrate in the filter or matrix is eluted or extracted from the filter or matrix at step 804. The concentrate is mixed with an electrophoresis buffer using a proper ratio at step 806. The mixture of antigens and electrophoresis buffer is loaded into a chamber at one end of a porous membrane at step 808. This may include, for example, the mixture of antigens and electrophoresis buffer being loaded into the sample chamber 502 at one end of the porous membrane 102. A high-voltage external electrophoresis field is applied across the porous membrane at step 810, and the electrophoresis is allowed to run to completion at step 812. The high-voltage external electrophoresis field may be created, for example, by the high-voltage power supply 106.

Because the antigens in the sample carry a negative charge upon mixing with the electrophoresis buffer, the antigens in the sample move towards the positive end of the porous membrane created by the high-voltage external electrophoresis field and come into contact with a binding region that contains antibodies specific for an antigen of interest. The binding region could be, for example, the binding region 110. The binding region is analyzed for the presence of the antigen of interest at step 814. The presence of the antigen of interest could be detected, for example, by spraying an ATP-releasing buffer and luciferin-luciferase reagent on the binding region. If the presence of the antigen of interest is detected, the quantity of the antigen of interest in the binding region is determined at step 816. The quantity of the antigens in the binding region can be determined, for example, by recording and analyzing the chemiluminescence data collected from luciferin-luciferase assay.

Although FIGS. 7 and 8 illustrate examples of methods for separating, detecting, and quantifying an antigen of interest, various changes may be made to FIGS. 7 and 8. For example, while shown as a series of steps, various steps in each figure could overlap, occur in parallel, occur in multiple times, or occur in a different order.

It may be advantageous to set forth definitions of certain words and phrases used throughout this patent document. The terms "include" and "comprise," as well as derivatives thereof, mean inclusion without limitation. The term "or" is inclusive, meaning and/or.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
    a porous membrane configured to retain antigens from a sample as the sample passes through the membrane; and
    a first binding region within a portion of the membrane, the first binding region comprising antibodies associated with a first antigen of interest;
    wherein the apparatus is configured such that at least some of the antigens retained in the membrane are moved across the membrane and brought into contact with the first binding region by applying an electrophoresis field across the membrane; and
    wherein the porous membrane is configured to permit the sample to pass through the porous membrane in a first direction and the apparatus is configured such that the electrophoresis field is applied across the porous membrane in a second direction that is substantially perpendicular to the first direction.

2. The apparatus of claim 1, wherein the first binding region is offset from a central portion of the porous membrane.

3. The apparatus of claim 1, further comprising:
    a second binding region within the porous membrane, the second binding region comprising antibodies associated with a second antigen of interest.

4. The apparatus of claim 1, wherein the porous membrane comprises at least one material selected from the group consisting of: polyvinylidene fluoride (PVDF), cellulose acetate (CA), polyether sulfone (PES), polysulfone (PS), and polyamide (PA).

5. The apparatus of claim 1, wherein the porous membrane has hydrophilic and low protein binding properties.

6. The apparatus of claim 5, wherein the porous membrane has a protein binding upper limit of 40-1000 ng/cm$^2$.

7. The apparatus of claim 1, wherein the porous membrane comprises a pore size from 0.2 μm to 10 μm.

8. A system comprising:
    a porous membrane configured to permit a sample to pass through the porous membrane;
    a binding region within a portion of the porous membrane, the binding region comprising antibodies associated with an antigen of interest;
    a voltage source configured to create an electrophoresis field to move a plurality of antigens in the sample across the porous membrane from a first area of the porous membrane to a second area of the porous membrane such that the antigens come into contact with the binding region; and
    a detector configured to detect if the antigen of interest is present in the binding region;
    wherein the porous membrane is configured to permit the sample to pass through the porous membrane in a first direction and the voltage source is configured to apply the electrophoresis field across the porous membrane in a second direction that is substantially perpendicular to the first direction.

9. The system of claim 8, wherein the detector comprises a reagent spraying unit.

10. The system of claim 8, wherein the detector comprises an optical detection unit.

11. The system of claim 8, wherein the porous membrane comprises an electrophoresis buffer.

12. The system of claim 8, wherein the porous membrane comprises at least one material selected from the group consisting of: polyvinylidene fluoride (PVDF), cellulose acetate (CA), polyether sulfone (PES), polysulfone (PS), and polyamide (PA).

13. The system of claim 8, wherein a presence of the antigen of interest is detected by exposing the binding region to a chemiluminescent reagent.

14. A method comprising:
    adding a sample to a chamber containing a porous membrane, a portion of the porous membrane comprising a first binding region having antibodies associated with a first antigen of interest;
    passing the sample through the porous membrane, the porous membrane retaining antigens from the sample as the sample passes through the membrane;
    applying an electrophoresis field across the porous membrane, wherein at least some of the antigens contained in the sample move across the porous membrane and come into contact with the first binding region; and
    detecting if the first antigen of interest is present in the first binding region;
    wherein the porous membrane permits the sample to pass through the porous membrane in a first direction and the electrophoresis field is applied across the porous membrane in a second direction that is substantially perpendicular to the first direction.

15. The method of claim 14, wherein detecting if the first antigen of interest is present comprises exposing the first binding region to a chemiluminescent reagent.

16. The method of claim 14, further comprising:
    determining a quantity of the first antigen of interest in the first binding region.

17. The method of claim 16, wherein determining the quantity of the first antigen of interest comprises performing a chemiluminescent assay on the first binding region.

18. The method of claim 14, further comprising:
    mixing the sample with an electrophoresis buffer prior to adding the sample to the chamber.

19. The method of claim 14, wherein the porous membrane further comprises a second binding region having antibodies associated with a second antigen of interest.

20. The method of claim 14, wherein the porous membrane further comprises a second binding region having antibodies associated with the first antigen of interest.

* * * * *